(12) United States Patent
Mang et al.

(10) Patent No.: US 11,937,036 B2
(45) Date of Patent: Mar. 19, 2024

(54) HEADSET

(71) Applicant: Andreas Stihl AG & Co. KG, Waiblingen (DE)

(72) Inventors: Harald Mang, Winnenden (DE); Maren Langhammer, Leutenbach (DE); Julian Danner, Großerlach (DE); Nils Conrad, Korb (DE)

(73) Assignee: Andreas Stihl AG & Co. KG, Waiblingen (DE)

( * ) Notice: Subject to any disclaimer, the term of this patent is extended or adjusted under 35 U.S.C. 154(b) by 110 days.

(21) Appl. No.: 17/536,034

(22) Filed: Nov. 28, 2021

(65) Prior Publication Data
US 2022/0174387 A1 Jun. 2, 2022

(30) Foreign Application Priority Data
Dec. 1, 2020 (EP) .................................... 20211095

(51) Int. Cl.
*H04R 1/10* (2006.01)
*A61F 11/14* (2006.01)
(Continued)

(52) U.S. Cl.
CPC ......... *H04R 1/1008* (2013.01); *H04R 1/1041* (2013.01); *A61F 11/14* (2013.01);
(Continued)

(58) Field of Classification Search
CPC ...... H04R 1/10; H04R 1/1008; H04R 1/1041; H04R 1/1075; H04R 1/1091;
(Continued)

(56) References Cited

U.S. PATENT DOCUMENTS 6,654,966 B2 * 12/2003 Rolla ................... H04R 5/0335
D14/206
2002/0080987 A1 * 6/2002 Almqvist ................ A61F 11/14
381/371
(Continued)

FOREIGN PATENT DOCUMENTS

EP 3 451 689 3/2019

OTHER PUBLICATIONS

HUSQVARNA: Husqvarna Zubehör und Bekleidung, catalogue published 2011, p. 22 showing pictures of various headsets.
(Continued)

*Primary Examiner* — Carolyn R Edwards
*Assistant Examiner* — Kuassi A Ganmavo
(74) *Attorney, Agent, or Firm* — Gudrun E. Huckett

(57) ABSTRACT

A headset has earmuffs connected by a connection element. The earmuffs have inner sides facing each other and outer sides facing away from each other in a first transverse direction. The earmuffs extend from a bottom side to a top side in a vertical direction. The earmuffs extend from a first to a second longitudinal side in a second transverse direction. At least one of the earmuffs has a positioning pocket at the outer side with a button arranged therein. The positioning pocket extends across a width in second transverse direction that corresponds to at least 50% of a width of the at least one of the earmuffs. The positioning pocket has a bottom end and a top end and extends in vertical direction from the bottom end to the top end. The top end of the positioning pocket forms a stop edge for fingertips of an operator's hand.

22 Claims, 4 Drawing Sheets

(51) Int. Cl.
*H04M 1/05* (2006.01)
*H04W 4/10* (2009.01)

(52) U.S. Cl.
CPC .............. *A61F 11/145* (2022.01); *H04M 1/05* (2013.01); *H04R 1/1075* (2013.01); *H04R 1/1091* (2013.01); *H04R 2201/107* (2013.01); *H04W 4/10* (2013.01)

(58) Field of Classification Search
CPC .. H04R 2201/107; H04W 4/10; A61F 11/145; A61F 11/14; H04M 1/05
See application file for complete search history.

(56) References Cited

U.S. PATENT DOCUMENTS

| | | | | |
|---|---|---|---|---|
| 2005/0238181 | A1* | 10/2005 | Nilsson | H04R 1/1083 381/72 |
| 2014/0193020 | A1* | 7/2014 | Krissman | H04R 1/1008 381/376 |
| 2016/0302029 | A1* | 10/2016 | Broadley | H04M 1/6058 |
| 2017/0048609 | A1* | 2/2017 | Schnell | H04R 25/43 |
| 2018/0302948 | A1* | 10/2018 | Kotlyarov | H04W 76/45 |
| 2019/0189106 | A1* | 6/2019 | Hull | H04R 1/1008 |
| 2019/0200125 | A1* | 6/2019 | Hilding | G10L 21/0232 |
| 2019/0342664 | A1* | 11/2019 | Payne | H04R 1/1008 |
| 2019/0387308 | A1* | 12/2019 | Lewis | H04R 1/1008 |
| 2023/0023459 | A1* | 1/2023 | Lindell | A61F 11/14 |

OTHER PUBLICATIONS

HUSQVARNA: Workshop manual X-COM R; Apr. 16, 2020.
HUSQVARNA: Operator's Manual X-Com R (HP310-1, HP310-2); Jul. 5, 2019.

* cited by examiner

HEADSET

BACKGROUND OF THE INVENTION

The invention relates to a headset comprising a first earmuff and a second earmuff, wherein the first earmuff and the second earmuff are connected to each other by a connection element. The earmuffs each comprise an inner side and an outer side, wherein the inner sides of the earmuffs are facing each other and the outer sides of the earmuffs are facing away from each other in a first transverse direction. The earmuffs each extend from their bottom side to their topside in a vertical direction and from there first longitudinal side to their second longitudinal side in a second transverse direction. The first earmuff and/or the second earmuff at its outer side comprises a positioning pocket with at least one button. The positioning pocket extends across a width in the second transverse direction of the earmuff, wherein the width of the positioning pocket corresponds to at least 50% of the width measured in the second transverse direction of the earmuff. The positioning pocket extends from a bottom end to a top end in the vertical direction of the earmuff.

EP 3 451 689 A1 discloses a headset comprising two earmuffs connected to each other by a headband. The headset is designed such that the operator can clamp the headset on his head by means of the headband, and the ears of the operator are covered by the earmuffs. On the one hand, the earmuffs provide hearing protection; on the other hand, the earmuffs are provided with speakers in order to transmit by means of a control interface information to the operator. Several buttons are provided at the earmuffs for operating the control interface.

A disadvantage of such headsets is that the buttons are difficult to find so that operation of the control interface is made difficult. Such headsets are in particular provided for working outdoors, for example, forest work, gardening or the like, when the operator wears usually work gloves. Wearing work gloves further makes difficult the action of pushing the corresponding buttons in a targeted fashion.

It is therefore an object of the invention to further develop a headset of the aforementioned kind such that a simple operation of the headset is enabled.

SUMMARY OF THE INVENTION

This object is achieved in accordance with the invention for a headset of the aforementioned kind in that the top end of the positioning pocket forms a stop edge as a rest for the fingertips of an operator.

The headset comprises a first earmuff and a second earmuff, wherein the first earmuff and the second earmuff are connected to each other by a connection element. The earmuffs comprise each an inner side and an outer side, wherein the inner sides of the earmuffs are facing each other and the outer sides of the earmuffs are facing away from each other in a first transverse direction. The earmuffs extend respectively from their bottom side to a top side in a vertical direction and from their first longitudinal side to their second longitudinal side in a second transverse direction. The first earmuff and/or the second earmuff comprises at its outer side a positioning pocket with at least one button, wherein the positioning pocket extends across a width in the second transverse direction of the earmuff, wherein the width of the positioning pocket amounts to at least 50% of the width of the earmuff measured in the second transverse direction. The positioning pocket extends in vertical direction of the earmuff from a bottom end to a top end. The top end of the positioning pocket forms a stop edge as a rest for the fingertips of an operator.

The operator can easily feel the stop edge of the positioning pocket with his fingers. The headset is configured in this context such that the operator can slide his hand into the positioning pocket until the fingertips of the operator contact the stop edge of the positioning pocket. Once the fingertips of the operator rest approximately at the stop edge of the positioning pocket, the hand is in a basic position. For this purpose, the operator can position his hand at the outer side near the bottom side of the earmuff and subsequently can slide his hand in vertical direction to the top side of the earmuff until the fingertips contact the stop edge of the positioning pocket. In this way, the hand of the operator can always be moved in a simple manner into the basic position from where the at least one button in the positioning pocket can be actuated. The stop edge of the positioning pocket forms thus a simple tactile orientation element so that the operation of the headset is possible without visual contact with the headset.

It is preferably provided that the stop edge comprises a depth which is measured in a first transverse direction from the inner side to the outer side of the earmuff, wherein the depth of the stop edge amounts to at least 5% of the depth of the earmuff measured in the first transverse direction. This configuration of the stop edge enables a simple tactile sensing of the stop edge. For example, it is possible for the operator, even when wearing gloves, to position his hand in the basic position by tactile sensing of the stop edge.

The bottom end of the positioning pocket preferably passes without shoulder or step into a base surface that forms the outer side of the earmuff. Due to the shoulder-free or step-free transition between the base surface of the earmuff and the positioning pocket, the hand of the operator can be pushed across the base surface into the positioning pocket.

It is advantageously provided that the positioning pocket in the second transverse direction of the earmuff is delimited by a first sidewall and a second sidewall, wherein the two sidewalls provide a guiding action in transverse direction of the earmuff for lateral guiding of the fingers of the operator. The first sidewall and the second sidewall of the positioning pocket form stops for the fingers of the operator in the second transverse direction. Already upon pushing the fingers into the positioning pocket, the fingers are guided by the sidewalls in vertical direction. When the hand of the operator is in the basic position, the hand is oriented on the earmuff by the stop edge of the positioning pocket in vertical direction and by the sidewalls in the second transverse direction.

It is preferably provided that in the positioning pocket of the first earmuff only a connection button is arranged that extends across at least 50% of the width of the positioning pocket. Accordingly, the at least one button of the first earmuff is configured as a connection button. Due to the wide configuration of the connection button, the operator can easily feel and actuate the connection button. The connection button is preferably provided for establishing a connection to a computer, in particular a smart phone.

It is preferably provided that in the positioning pocket of the second earmuff at least two buttons, in particular three buttons, are arranged. Advantageously, the at least two buttons, respectively, the at least three buttons, are separated from each other by a separation web. In this way, the operator can differentiate the buttons in a simple way. Preferably, one of the at least two buttons is recessed relative to the other button in the direction toward the inner side of the earmuff in the positioning pocket. The depth displacement of the buttons relative to each other also enables the operator to differentiate in a simple manner between the buttons. Advantageously, the at least one button comprises a collar which at least partially is circumferentially arranged around the button.

It is preferably provided that a lateral button is arranged at the first earmuff and/or at the second earmuff outside of the positioning pocket wherein the lateral button and the positioning pocket are arranged relative to each other such that, in a basic position of the hand of the operator, the at least one button in the positioning pocket and the lateral button can be actuated without having to reposition the hand. Preferably, in the basic position of the hand of the operator, three buttons in the positioning pocket and the lateral button can be actuated without having to reposition the hand. In this way, a particularly ergonomic operation of the headset is possible.

Preferably, the lateral button is arranged between the bottom side of the earmuff and the second longitudinal side of the earmuff. In this way, the lateral button can be actuated by the thumb in a simple manner.

It is advantageously provided that, in a viewing direction along the first transverse direction looking onto the outer side, the earmuff comprises a first center of area and the lateral button comprises a second center of area, wherein the distance measured in vertical direction between the first center of area and the second center of area corresponds to at least 20%, in particular at least 30%, preferably approximately 35%, of the height of the earmuff. The first center of area of the earmuff is positioned preferably on the positioning pocket, in particular on the at least one button. Due to the distance between the two centers of area, an ergonomic arrangement of the lateral button to the at least one button in the positioning pocket is ensured. This enables the operator to actuate in the basic position of the hand the at least one button with the index finger, middle finger and/or ring finger and to actuate additionally also the lateral button by the thumb in the basic position in a comfortable manner.

Advantageously, the lateral button of the first earmuff comprises three knob-shaped elevations. In this way, the lateral button of the first earmuff can be differentiated from the lateral button of the second earmuff.

Preferably, the lateral button of the second earmuff is embodied as a circular function button, in particular as a push-to-talk button or a mute button. By actuation of the lateral button of the first earmuff or the lateral button of the second earmuff, a communication-related function can be activated or deactivated, in particular a push-to-talk function for a radio communication device connectable to the headset or a function for a group communication or a microphone muting.

BRIEF DESCRIPTION OF THE DRAWING

Further features of the invention result from the specification and the drawing in which an embodiment of the invention described in detail in the following is represented.

DESCRIPTION OF THE PREFERRED EMBODIMENTS

Figure 1:
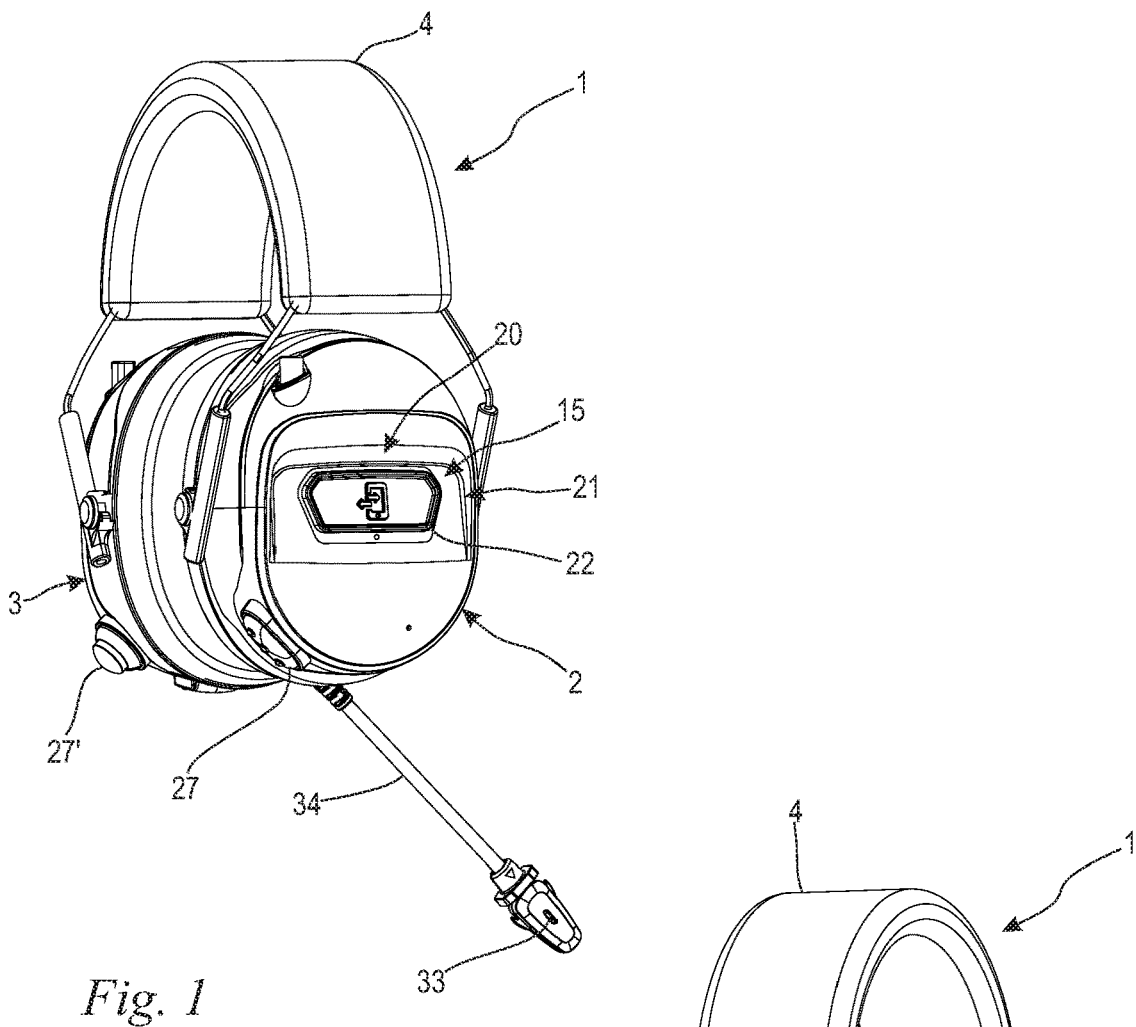
FIG. 1 is a perspective illustration of the first earmuff of a headset according to the invention.

FIG. 1 illustrates a headset 1 according to the invention. The headset 1 serves inter alia as a hearing protection when working at correspondingly high noise emissions. This includes, for example, working with motor chainsaws, brush cutters, trimmers, blowers, cut-off machines, stone cutters and the like. The headset 1 comprises a first earmuff 2, a second earmuff 3, and a connection element 4. The first earmuff 2 and the second earmuff 3 are connected to each other by the connection element 4. In the illustrated embodiment, the connection element 4 is designed as an elastic headband. The headband is at least partially encased by padding for increasing the wearing comfort of the headset 1. In an alternative embodiment, not illustrated, of the headset 1, the connection element 4 can be designed also as a protective helmet or the like. In such an embodiment, the first earmuff 2 and the second earmuff 3 are secured by fastening elements to the protective helmet.

The first earmuff 2 and the second earmuff 3 each comprise a speaker, not illustrated, wherein the speaker is arranged in the earmuffs 2, 3, respectively. In addition, the headset 1 comprises a microphone 33 that is fastened by a holder 34 at one of the two earmuffs 2, 3. The holder 34 is preferably attached at the second earmuff 3. However, it can also be expedient to secure the holder 34 with microphone 33 at the first earmuff 2. Preferably, both earmuffs 2, 3 are provided with receptacles 35 for the holder 34 so that the operator can fasten the holder 34 either at the first earmuff 2 or at the second earmuff 3. The holder 34 is designed such that it holds the microphone 33 closer to the mouth of the operator when the operator wears the headset 1 as intended.

Figure 3:
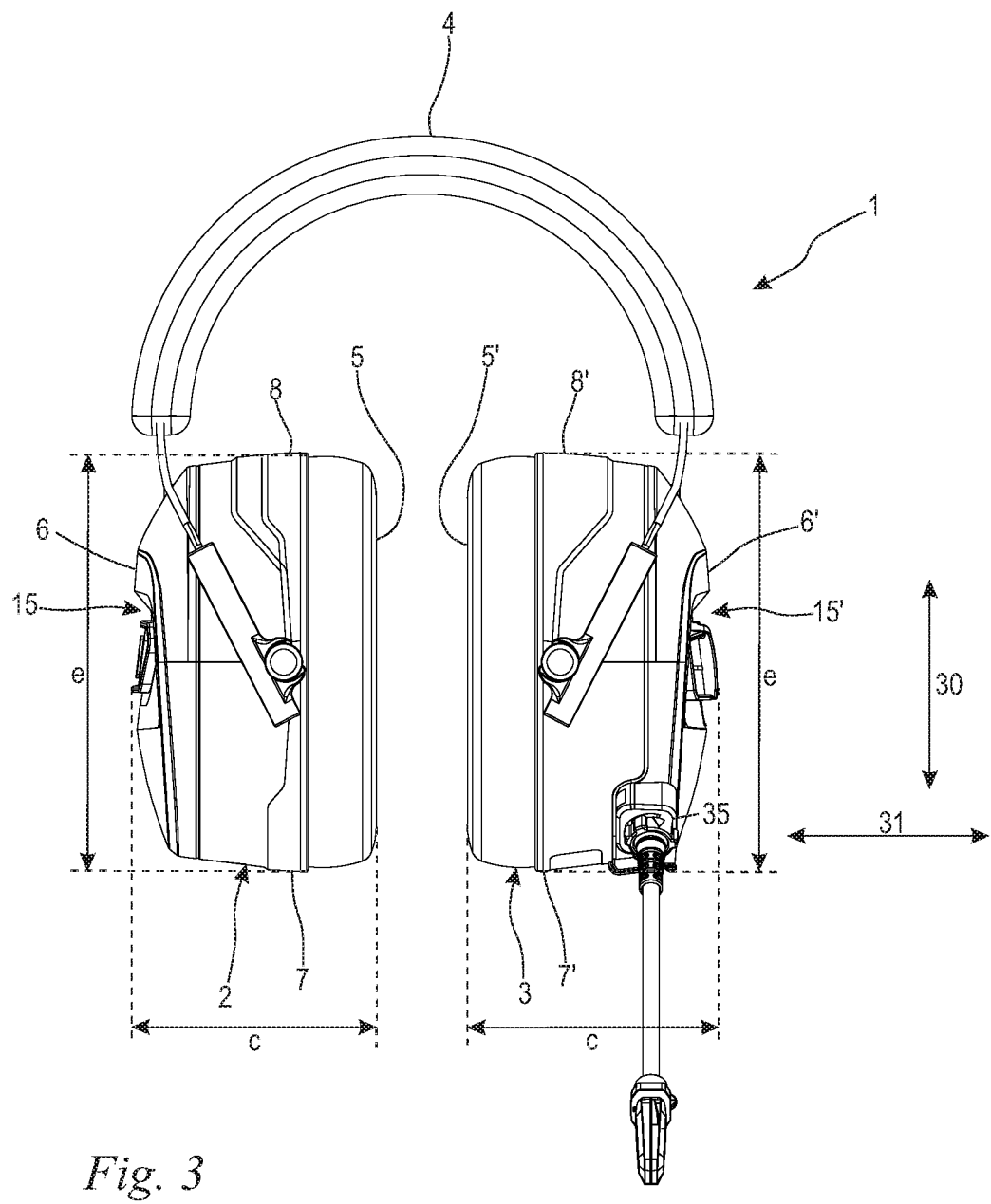
FIG. 3 is a front view of the headset according to FIG. 1.

As shown in FIG. 3, the first earmuff 2 and the second earmuff 3 each comprise an outer side 6, 6' and each comprise an inner side 5, 5'. The inner sides 5, 5' of the earmuffs 2, 3 are facing each other, the outer sides 6, 6' of the earmuffs 2, 3 are facing away from each other. The earmuffs 2, 3 extend each from their inner side 5, 5' to the outer side 6, 6' in a first transverse direction 31.

Figure 4:
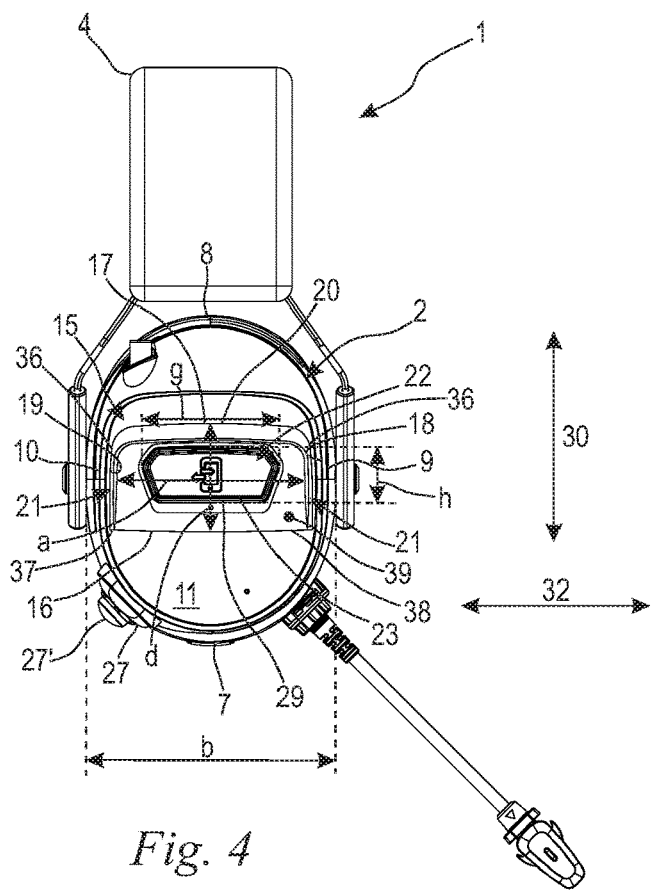
FIG. 4 is a side view of the first earmuff of the headset according to FIG. 1.
Figure 5:
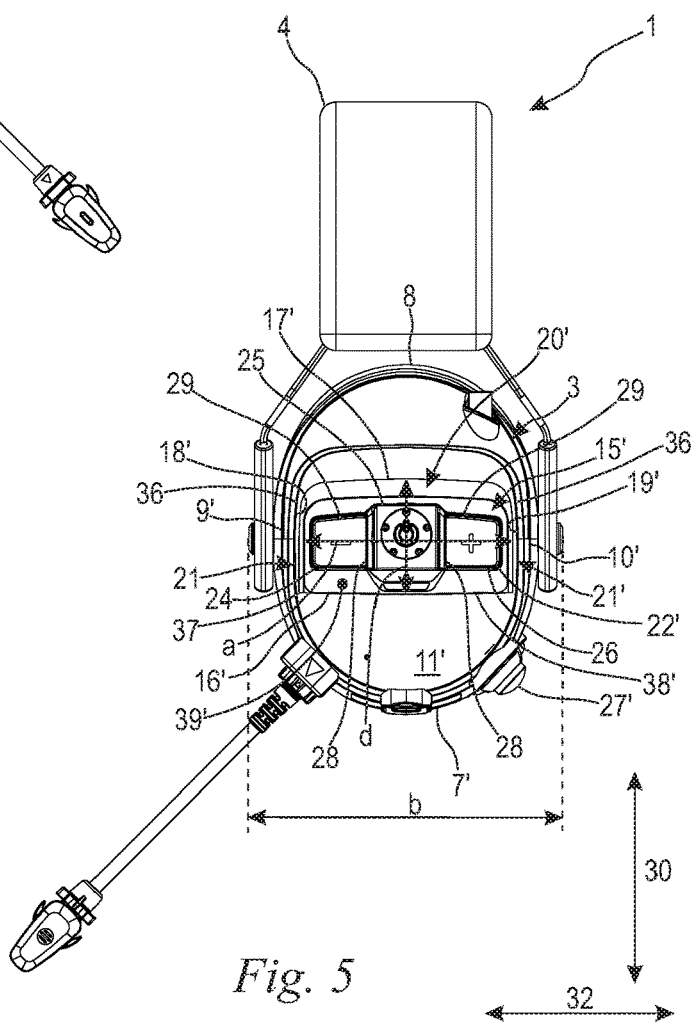
FIG. 5 is a side view of the second earmuff of the headset according to FIG. 1.

As illustrated in FIGS. 4 and 5, the earmuffs 2, 3 are approximately oval in the embodiment in viewing direction of FIGS. 4 and 5, i.e., in viewing direction of the first transverse direction 31. Other shapes of the earmuffs 2, 3 can also be expedient. The earmuffs 2, 3 have correlated therewith the individual sides as explained in the following.

As illustrated in FIG. 3, the earmuffs 2, 3 extend from their bottom side 7, 7' to the top side 8, 8' in a vertical direction 30. The topside 8, 8' is the side of the earmuff 2, 3 that is facing away from the holder 34; the bottom side 7, 7' is the side of the earmuffs 2, 3 which is facing the holder 34. As illustrated in FIGS. 4 and 5, the earmuffs 2, 3 extend from a first longitudinal side 9, 9' to the second longitudinal side 10, 10' in a second transverse direction 32. The first longitudinal side 9, 9' of the earmuff 2, 3 is the side which is facing the microphone 33, the second longitudinal side 10, 10' of the earmuff 2, 3 is the side which is facing away from the microphone 33. In the embodiment, the first transverse direction 31, the second transverse direction 32, and the vertical direction 30 of the headset 1 are oriented perpendicularly to each other, respectively. Accordingly, the first transverse direction 31, the second transverse direction 32, and the vertical direction 30 at least in regard to their orientation correspond to a straight orthogonal coordinate system (Cartesian coordinate system).

Figure 2:
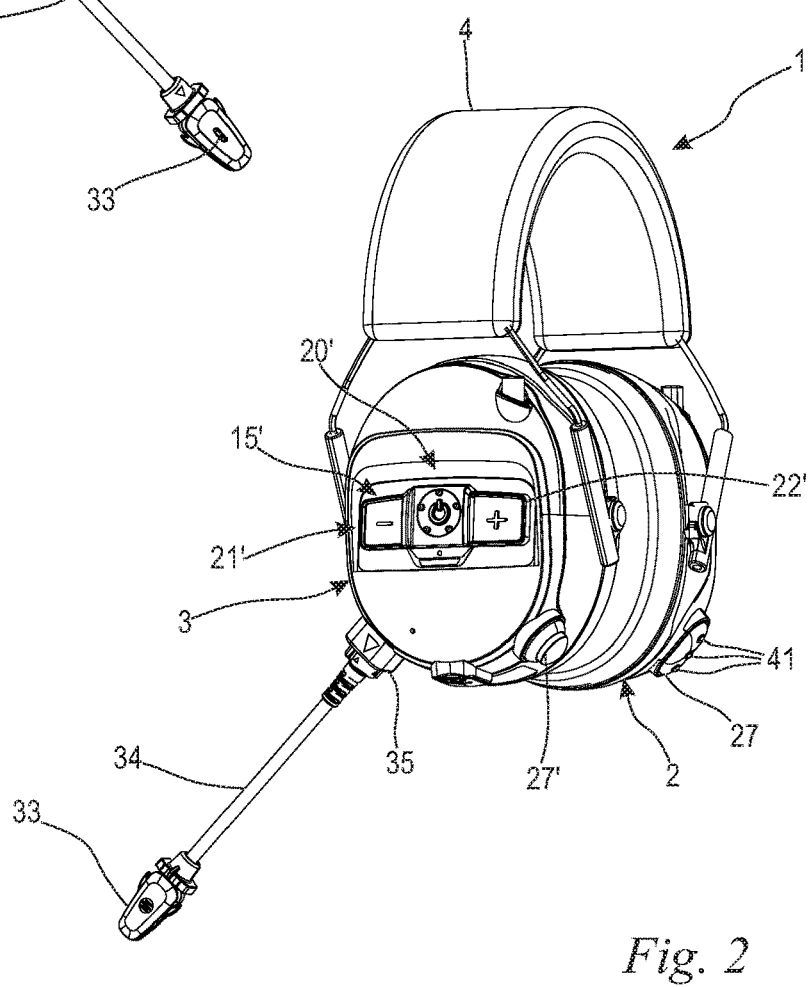
FIG. 2 is a perspective illustration of the second earmuff of the headset according to FIG. 1.

FIGS. 1 and 2 illustrates that, in the embodiment of the headset 1 in accordance with the invention, both earmuffs 2, 3 comprises a positioning pocket 15, 15', respectively, for simple positioning of the hand of the user. It can also be expedient that only the first earmuff 2 or the second earmuff 3 comprises a positioning pocket 15, 15'. The positioning pocket 15, 15' is arranged at the outer side 6, 6' of the earmuff 2, 3. At least one button 22, 22' is arranged in the positioning pocket 15, 15'.

As illustrated in FIGS. 4 and 5, the positioning pocket 15, 15' comprises a stop edge 20, 20'. The stop edge 20, 20' extends in the second transverse direction 32. The stop edge 20, 22 is designed such that the fingertips contact and impact on the stop edge 20, 20' upon insertion into the positioning pocket 15, 15' in vertical direction 30. Moreover, the positioning pocket 15, 15' comprises a first sidewall 18, 18' and a second sidewall 19, 19'. The sidewalls 18, 18', 19, 19' extend approximately in vertical direction 30. The first sidewall 18, 18' and the second sidewall 19, 19' comprises each a first end 36 which is facing the topside 8, 8' of the earmuff 2, 3. The first sidewall 18, 18' and the second sidewall 19, 19' are connected to each other by the stop edge 20, 20'. The stop edge 20, 20' adjoins the first ends 36 of the two sidewalls 18, 18', 19, 19'. The sidewalls 18, 18', 19, 19' form a guide 21, 21' for the fingers of the operator in vertical direction 30. Due to the guide 21, 21', the fingers are positioned in the second transverse direction 32. In addition, sliding off of the fingers in the second transverse direction 32 is avoided.

As is illustrated in FIGS. 4 and 5, the positioning pocket 15, 15' has a width a which corresponds to the distance of the two sidewalls 18, 18', 19, 19' measured in the second transverse direction 32. The earmuff 2, 3 comprises a width b which corresponds to the maximum distance between the first longitudinal side 9, 9' and the second longitudinal side 10, 10' of the earmuff 2, 3 measured in the second transverse direction 32. The width a of the positioning pocket 15 amounts to at least 50%, in particular at least 60%, preferably approximately 75% of the width b of the earmuff 2, 3.

As illustrated in FIGS. 4 and 5, the positioning pocket 15, 15' comprises a height d which corresponds to the distance measured in the vertical direction 30 between a bottom end 16, 16' and a top end 17, 17' of the positioning pocket 15, 15'. The top end 17, 17' of the positioning pocket 15, 15' is formed by the stop edge 20, 20' of the positioning pocket 15, 15'. The bottom end 16, 16' of the positioning pocket 15, 15' is the section of the earmuff 2, 3 in which the positioning pocket 15, 15' passes into a base surface 11, 11' of the earmuff 2, 3 that forms the outer side 6, 6' of the earmuff 2, 3. In the present embodiment, this section is formed by a shoulder-free or step-free edge 38, 38' between a bottom surface 39, 39' of the positioning pocket 15, 15' and the base surface 11, 11' of the earmuff 2, 3. It can also be expedient to provide, instead of the edge 38, 38', a smooth transition between the bottom surface 39, 39' of the positioning pocket 15, 15' and the base surface 11, 11' of the earmuff 2, 3. In addition, in the embodiment, the bottom end 16, 16' of the positioning pocket 15, 15' is also defined by the second ends 37 of the sidewalls 18, 18', 19, 19' of the positioning pocket 15, 15', which second ends 37 are facing the bottom side 7, 7' of the earmuff 2, 3. The earmuff 2, 3 has a height e which corresponds to the maximum distance measured in the vertical direction 30 between the bottom side 7, 7' and the top side 8, 8' of the earmuff 2, 3. The height d of the positioning pocket 15, 15' amounts to at least 15%, in particular at least 25%, preferably approximately 30%, of the height e of the earmuff 2, 3.

In the embodiment, the bottom surface 39, 39' of the positioning pocket 15, 15' is slightly convexly curved. As illustrated schematically in FIG. 6, an approximation plane 40 is shown which approximates the bottom surface 39, 39' of the positioning pocket 15, 15'. In the side view of the first earmuff 2 according to FIG. 6, the illustration of a button 22 has been omitted in order to better represent the bottom surface 39. The approximation plane 40 is positioned in relation to the inner side 5, 5' of the earmuff 2, 3 at an angle α which opens toward the bottom side 7, 7' of the earmuff 2, 3. In the embodiment, the angle α amounts to at least 5°, in particular approximately 7°. In an alternative embodiment, it can also be expedient to orient the bottom surface 39, 39' or its approximation plane 40 and the inner side 5, 5' of the earmuff 2, 3 approximately parallel to each other.

Figure 6:
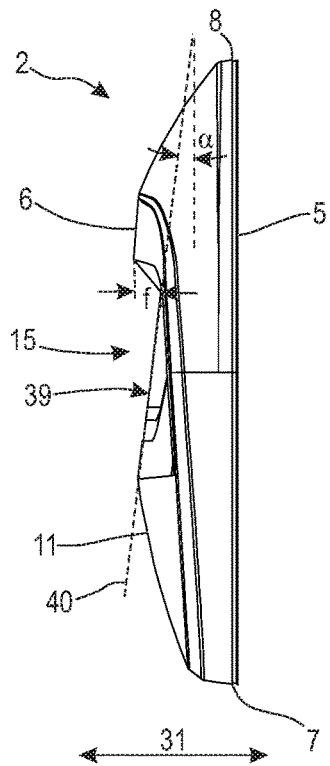
FIG. 6 is a side view of a schematic detail illustration of the first earmuff without button.

As illustrated in FIG. 6, the stop edge 20, 20' has a depth f that corresponds to the maximum distance measured in the first transverse direction 31 between the base surface 11 of the earmuff 2, 3 and the bottom surface 39, 39' of the positioning pocket 15, 15'. The earmuff 2, 3 comprises a depth c (FIG. 3) that corresponds to the maximum distance measured in the first transverse direction 31 between the inner side 5, 5' and the outer side 6, 6' of the earmuff 2, 3. In the embodiment, the depth f of the stop edge 20, 20' amounts to at least 5% of the depth c of the earmuff 2, 3.

The headset 1 comprises moreover a control interface, not illustrated, in order to be able to control various devices by means of the headset 1 or to be able to perform functions of the headset 1. By means of the control interface, the headset 1 is connectable to a computer, in particular to a smart phone, a tablet, a notebook or the like. Moreover, the embodiment of the headset 1 comprises a radio, a music player and/or the like. In the illustrated embodiment, the headset 1 is configured for connection to a radio communication device.

As illustrated in FIG. 4, only one button 22 is arranged in the positioning pocket 15, 15' of the first earmuff 2, 3. The button 22 is designed as a connection button 23. The connection button 23 enables the operator to connect the headset 1 to a computer, in particular to a smart phone, tablet, notebook or the like. Preferably, the radio can also be activated by means of the connection button 23. When the headset 1 is connected to the computer, calls can be received and ended and voice assistants for operating further applications can be activated preferably by means of the connection button 23. It can be advantageous to assign additional functions to the connection button 23.

As is illustrated in FIG. 4, the connection button 23 comprises a width g measured in the second transverse direction 32 that corresponds to at least 50%, in particular at least 60%, preferably approximately 75%, of the width a of the positioning pocket 15, 15'. Moreover, the width g of the connection button 23 corresponds to at least 25%, preferably at least 35%, in particular at least 45% of the width b of the earmuff 2, 3. The connection button 23 comprises a height h measured in vertical direction 30 that corresponds to at least 30%, in particular at least 40%, preferably approximately 50%, of the height d of the positioning pocket 15, 15'. In the embodiment, the connection button 23 comprises an upright collar 29 circumferentially arranged about the connection button 23. The collar 29 enables a simple tactile sensing of the connection button 23.

As illustrated in FIG. 4, the first earmuff 2 comprises a lateral button 27. The lateral button 27 of the first earmuff 2 in the embodiment is arranged between the bottom side 7 of the first earmuff 2 and the second longitudinal side 10 of the earmuff 2. On the lateral button 27 of the first earmuff 2, three knob-type elevations 41 are provided. In the embodiment, the elevations are arranged in a row. Due to the knob-type elevations 41, the operator can easily recognize the lateral button 27. In the preferred embodiment of the headset 1, the microphone 33 can be activated and deactivated by means of the lateral button 27 of the first earmuff 2. Preferably, also a group communication with other operators who wear such a headset 1 can be activated or deactivated by switching the microphone 33 on and off. The lateral button 27 is arranged relative to the positioning pocket 15 as well as the corresponding connection button 23 such that, after placing the hand of the operator in the basic position, the operator can actuate the connection button 23 with his index finger, middle finger and/or ring finger and the lateral button 27 with this thumb. The hand must not be moved to do this. In this way, an ergonomic operation of the first earmuff 2 is ensured. The hand of the operator is in the basic position when the fingertips of the operator are approximately contacting the stop edge 20, 20' of the positioning pocket 15, 15'.

As illustrated in FIG. 5, three buttons 24, 25, 26 are arranged in the positioning pocket 15' of the second earmuff 3. The three buttons 24, 25, 26 are a first button 24, a second button 25, and a third button 26. The three buttons 24, 25, 26 are arranged adjacent to each other in the second transverse direction 32. In this way, the operator, in the basic position of his hand, can place one finger on each one of the three buttons 24, 25, 26 so that the operation of the buttons 24, 25, 26 is simplified. The second button 25 is arranged between the first button 24 and the third button 26. In an alternative embodiment, it can also be expedient to provide a different number of buttons in the positioning pocket 15'. The second button 25 is displaced relative to the first button 24 and the third button 26 in the first transverse direction 31, in particular is elevated. The second button 25 is separated respectively by a separation web 28 from the first button 24 and from the third button 26. The separation web 28 enables the operator to haptically differentiate the three buttons 24, 25, 26 in their spatial arrangement in a simple manner. In addition, the first button 24 and the third button 26 are at least partially surrounded at their circumference by an upright collar 29. The collar 29 of the first button 24 and of the third button 26 adjoins respectively the separation web 28. The collar 29 of the first button 24 and of the third button 26 enable the operator to easily recognize the buttons.

In the embodiment, the volume of the speakers in the two earmuffs 2, 3 can be preferably adjusted by means of the first button 24 and the third button 26. In addition, the radio can be activated and deactivated by means of the third button 26. The headset 1 can be switched on by means of the second button 25.

Preferably, by means of the second button 25, the headset 1 can also be coupled to the computer, i.e., a smart phone or the like. Moreover, the second button 25 in the embodiment is preferably also used for navigation when playing music as well as for selecting radio stations when using the radio.

As illustrated in FIG. 5, the second earmuff 3 comprises a lateral button 27'. In the embodiment, the lateral button 27' of the second earmuff 3 is arranged between the bottom side 7' of the second earmuff 3 and the first longitudinal side 9' of the second earmuff 3. The lateral button 27' comprises in the embodiment a circular basic shape (FIG. 1). Since the lateral button 27 of the first earmuff 2 and the lateral button 27' of the second earmuff 3 are differently designed, the two lateral buttons 27, 27' can be easily differentiated by the operator. In the preferred embodiment of the headset 1, the lateral button 27' is embodied as a communication-relevant function button, in particular a push-to-talk button or a mute button.

As illustrated in FIG. 5, the lateral buttons 27' of the second earmuff 3 and the buttons 24, 25, 26 in the positioning pocket 15' are arranged such that the three buttons 24, 25, 26 as well as the lateral button 27 can be actuated from the basic position of the hand of the operator. Preferably, in the basic position of the hand, the first button 24 can be actuated by the ring finger, the second button 25 by the middle finger, the third button 26 by the index finger, and the lateral button 27' by the thumb. Thus, all buttons can be actuated from the basic position of the hand without having to reposition the hand.

Figure 7:
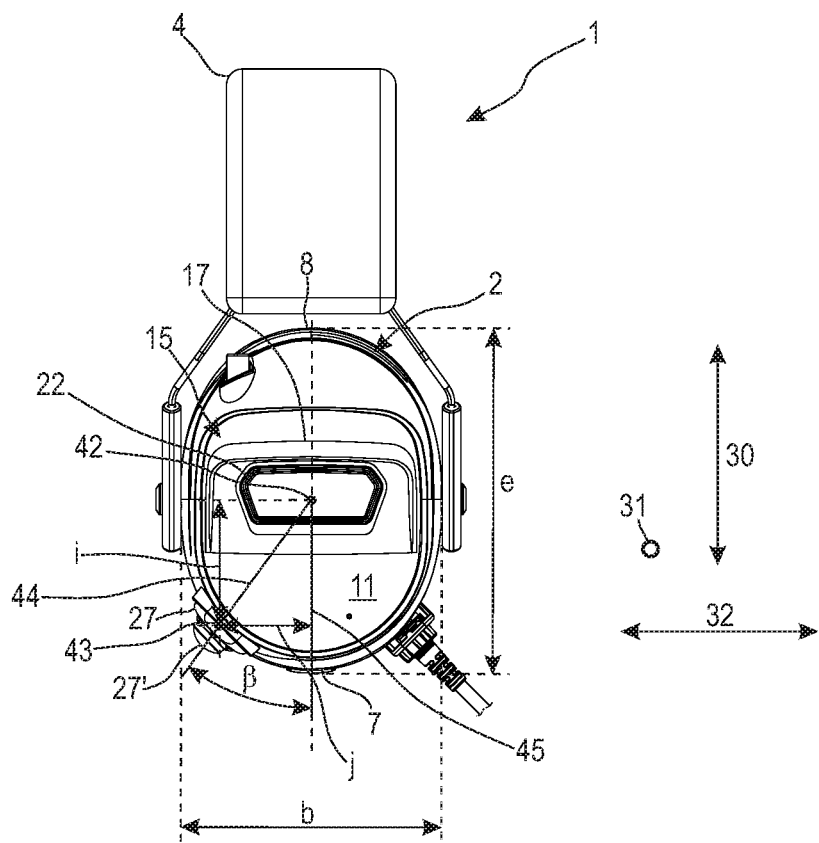
FIG. 7 is a detail side view of the first earmuff of the headset according to FIG. 1.

In FIG. 7, the headset 1 according to the invention is illustrated in a detail side view of the first earmuff 2. The first earmuff 2 comprises a first center of area 42 looking in the viewing direction along the first transverse direction 31 toward the outer side 6. In the embodiment, the first center of area 42 is arranged in particular approximately centrally on the positioning pocket 15. In the embodiment, the first center of area 42 is arranged in particular approximately centrally on the at least one button 22. The lateral button 27 of the earmuff 2 comprises a second center of area 43 in the viewing direction along the first transverse direction 31 onto the outer side 6. The first center of area 42 of the first earmuff 2 and the second center of area 43 of the lateral button 27 have a distance i that is measured in the vertical direction 30 wherein the distance i corresponds to at least 20%, in particular at least 30%, preferably approximately 35%, of the height e of the earmuff 2. The first center of area 42 of the first earmuff 2 and the second center of area 43 of the lateral button 27 comprise a distance j measured in the second transverse direction 32, wherein the distance j corresponds to at least 20%, in particular at least 30%, preferably approximately 35%, of the width b of the earmuff 2. As shown in FIG. 7, a longitudinal straight line 45 oriented in vertical direction 30 extends through the first center of area 42 of the earmuff 2. Moreover, a connection straight line 44 is illustrated which extends through the first center of area 42 and through the second center of area 43 and intercepts the longitudinal straight line 45 at the same time. As illustrated in FIG. 7, the longitudinal straight line 45 and the connection straight line 44 are positioned at an angle β to each other, wherein the angle β opens toward the bottom side 7 of the first earmuff 2. The angle β is in a range of 15° to 60°, preferably of 25° to 45°, in the embodiment. The angle β amounts to preferably approximately 35°.

In regard to their basic shape, the first earmuff 2 and the second earmuff 3 are substantially mirror-symmetrically embodied relative to a plane which is defined by the vertical direction 30 and the second transverse direction 32. Therefore, the afore described conditions of the arrangement of the lateral button 27 to the center of area 42 of the first earmuff 2 also apply to the second earmuff 3.

The specification incorporates by reference the entire disclosure of European priority document 20 211 095.3 having a filing date of Dec. 1, 2020.

While specific embodiments of the invention have been shown and described in detail to illustrate the inventive principles, it will be understood that the invention may be embodied otherwise without departing from such principles.

What is claimed is:

1. A headset comprising:
a first earmuff and a second earmuff;
a connection element connecting the first earmuff and second earmuff to each other;
wherein the first and second earmuffs each have an inner side and an outer side, wherein the inner sides of the first and second earmuffs are facing each other in a first transverse direction, and wherein the outer sides of the first and second earmuffs are facing away from each other in the first transverse direction;
wherein the first and second earmuffs each comprise a bottom side and a top side and each extend from the bottom side to the top side in a vertical direction;
wherein the first and second earmuffs each comprise a first longitudinal side and a second longitudinal side and each extend from the first longitudinal side to the second longitudinal side in a second transverse direction;
wherein at least one of the first and second earmuffs comprises a positioning pocket arranged at the outer side of the at least one of the first and second earmuffs;
wherein a button is arranged in the positioning pocket;
wherein the positioning pocket extends across a width in the second transverse direction, wherein the width of the positioning pocket corresponds to at least 50% of a width of the at least one of the first and second earmuffs measured in the second transverse direction;
wherein the positioning pocket comprises a bottom end and a top end, wherein the positioning pocket extends in the vertical direction from the bottom end to the top end;
wherein the top end of the positioning pocket forms a stop edge providing a rest for fingertips of a hand of an operator;
wherein the stop edge comprises a depth measured in the first transverse direction, wherein the depth of the stop edge corresponds to a maximum distance measured in the first transverse direction between a base surface forming the outer side of the at least one of the first and second earmuffs and a bottom surface of the positioning pocket;
wherein the at least one of the first and second earmuffs comprises a depth corresponding to a maximum distance measured in the first transverse direction between the inner side and the outer side of the at least one of the first and second earmuffs;
wherein the depth of the stop edge amounts to at least 5% of the depth of the at least one of the first and second earmuffs.

2. The headset according to claim 1, wherein the button arranged in the positioning pocket is a connection button, wherein the connection button extends across at least 50% of the width of the positioning pocket and is the only button arranged in the positioning pocket.

3. The headset according to claim 2, wherein the connection button is configured to connect the head set to a computer.

4. The headset according to claim 3, wherein the computer is a smart phone.

5. The headset according to claim 1, wherein two or more of said button are arranged in the positioning pocket.

6. The headset according to claim 5, wherein the two or more buttons are separated from each other by a separation web, respectively.

7. The headset according to claim 5, wherein the two or more buttons include a first button and a second button, wherein the first button is recessed relative to the second button in the positioning pocket in a direction toward the inner side of the at least one of the first and second earmuffs.

8. The headset according to claim 1, wherein the at least one of the first and second earmuffs comprises a lateral button arranged outside of the positioning pocket, wherein an arrangement of the lateral button and of the positioning pocket relative to each other is configured to enable the operator, in a basic position of the hand of the operator on the at least one of the first and second earmuffs, to actuate the button arranged in the positioning pocket and the lateral button without having to reposition the hand.

9. The headset according to claim 8, wherein the positioning pocket comprises three of said button, wherein the arrangement of the lateral button and of the positioning pocket relative to each other is such that the three buttons arranged in the positioning pocket and the lateral button are actuatable by the operator without having to reposition the hand.

10. The headset according to claim 8, wherein the lateral button is arranged between the bottom side and the second longitudinal side of the at least one of the first and second earmuffs.

11. The headset according to claim 8, wherein, in a viewing direction looking on the outer side of the at least one of the first and second earmuffs along the first transverse direction, the at least one of the first and second earmuffs comprises a first center of area and the lateral button comprises a second center of area, wherein a distance measured in the vertical direction between the first center of area and the second center of area amounts to at least 20% of a height of the at least one of the first and second earmuffs measured in the vertical direction.

12. The headset according to claim 11, wherein the distance amounts to at least 30%.

13. The headset according to claim 8, wherein the lateral button comprises three knob-type elevations.

14. The headset according to claim 8, wherein the lateral button is a circular function button.

15. The headset according to claim 14, wherein the circular function button is a push-to-talk button or a mute button.

16. The headset according to claim 8, wherein the lateral button of the first earmuff comprises three knob-type elevations and wherein the lateral button of the second earmuff is a circular function button.

17. The headset according to claim 16, wherein the circular function button is a push-to-talk button or a mute button.

18. The headset according to claim 1, wherein the button arranged in the positioning pocket of the first earmuff is a connection button, wherein the connection button extends across at least 50% of the width of the positioning pocket of the first earmuff and is the only button arranged in the positioning pocket of the first earmuff, wherein in the positioning pocket of the second earmuff a plurality of said button are arranged and the plurality of said button are separated from each other by a separation web, respectively.

19. The headset according to claim 18, wherein the connection button is configured to connect the head set to a computer.

20. The head set according to claim 1, wherein the stop edge is a stop surface.

21. A headset comprising:
a first earmuff and a second earmuff;
a connection element connecting the first earmuff and second earmuff to each other;

wherein the first and second earmuffs each have an inner side and an outer side, wherein the inner sides of the first and second earmuffs are facing each other in a first transverse direction, and wherein the outer sides of the first and second earmuffs are facing away from each other in the first transverse direction;

wherein the first and second earmuffs each comprise a bottom side and a top side and each extend from the bottom side to the top side in a vertical direction;

wherein the first and second earmuffs each comprise a first longitudinal side and a second longitudinal side and each extend from the first longitudinal side to the second longitudinal side in a second transverse direction;

wherein at least one of the first and second earmuffs comprises a positioning pocket arranged at the outer side of the at least one of the first and second earmuffs;

wherein a button is arranged in the positioning pocket;

wherein the positioning pocket extends across a width in the second transverse direction, wherein the width of the positioning pocket corresponds to at least 50% of a width of the at least one of the first and second earmuffs measured in the second transverse direction;

wherein the positioning pocket comprises a bottom end and a top end, wherein the positioning pocket extends in the vertical direction from the bottom end to the top end;

wherein the top end of the positioning pocket forms a stop edge providing a rest for fingertips of a hand of an operator;

wherein the bottom end of the positioning pocket passes without a shoulder or step into the outer side of the at least one of the first and second earmuffs.

22. A headset comprising:

a first earmuff and a second earmuff;

a connection element connecting the first earmuff and second earmuff to each other;

wherein the first and second earmuffs each have an inner side and an outer side, wherein the inner sides of the first and second earmuffs are facing each other in a first transverse direction, and wherein the outer sides of the first and second earmuffs are facing away from each other in the first transverse direction;

wherein the first and second earmuffs each comprise a bottom side and a top side and each extend from the bottom side to the top side in a vertical direction;

wherein the first and second earmuffs each comprise a first longitudinal side and a second longitudinal side and each extend from the first longitudinal side to the second longitudinal side in a second transverse direction;

wherein at least one of the first and second earmuffs comprises a positioning pocket arranged at the outer side of the at least one of the first and second earmuffs;

wherein a button is arranged in the positioning pocket;

wherein the positioning pocket extends across a width in the second transverse direction, wherein the width of the positioning pocket corresponds to at least 50% of a width of the at least one of the first and second earmuffs measured in the second transverse direction;

wherein the positioning pocket comprises a bottom end and a top end, wherein the positioning pocket extends in the vertical direction from the bottom end to the top end;

wherein the top end of the positioning pocket forms a stop edge providing a rest for fingertips of a hand of an operator;

wherein the positioning pocket is delimited in the second transverse direction by a first sidewall and a second sidewall, wherein the first sidewall and the second sidewall provide a guide in the second transverse direction for lateral guiding of fingers of the hand of the operator.

* * * * *